US011975007B2

(12) United States Patent
Nowotny et al.

(10) Patent No.: US 11,975,007 B2
(45) Date of Patent: May 7, 2024

(54) MEDICAMENTS CONTAINING RIBOFLAVIN EXHIBITING IMPROVED FLOWABILITY

(71) Applicant: DSM IP Assets B.V., Heerlen (NL)

(72) Inventors: Markus Nowotny, Kaiseraugst (CH); Zdravka Misic, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 314 days.

(21) Appl. No.: 17/291,073

(22) PCT Filed: Oct. 9, 2019

(86) PCT No.: PCT/EP2019/077270
§ 371 (c)(1),
(2) Date: May 4, 2021

(87) PCT Pub. No.: WO2020/094319
PCT Pub. Date: May 14, 2020

(65) Prior Publication Data
US 2021/0401847 A1 Dec. 30, 2021

(30) Foreign Application Priority Data

Nov. 7, 2018 (EP) ..................................... 18204934
Nov. 7, 2018 (EP) ..................................... 18204935

(51) Int. Cl.
| *A61K 31/525* | (2006.01) |
| *A61K 9/00* | (2006.01) |
| *A61K 9/14* | (2006.01) |
| *A61K 31/277* | (2006.01) |
| *A61K 31/4422* | (2006.01) |
| *A61K 31/554* | (2006.01) |

(52) U.S. Cl.
CPC .......... *A61K 31/525* (2013.01); *A61K 9/0053* (2013.01); *A61K 9/14* (2013.01); *A61K 31/277* (2013.01); *A61K 31/4422* (2013.01); *A61K 31/554* (2013.01)

(58) Field of Classification Search
None
See application file for complete search history.

(56) References Cited

U.S. PATENT DOCUMENTS

| 4,904,699 A | 2/1990 | Bauer |
| 5,034,389 A | 7/1991 | Gyure et al. |
| 5,300,303 A | 4/1994 | Grimmer et al. |
| 5,998,448 A | 12/1999 | Lesur et al. |
| 6,093,715 A | 7/2000 | Harz et al. |
| 2008/0207624 A1 | 8/2008 | Sugita et al. |

FOREIGN PATENT DOCUMENTS

| CN | 1274579 | 11/2000 |
| CN | 104434823 | 3/2015 |
| DE | 195 15 971 | 11/1996 |
| JP | 63-165318 | 7/1988 |
| JP | H5-501397 | 5/1993 |
| JP | H11-504907 | 5/1999 |
| WO | 91/01731 | 2/1991 |
| WO | WO 2005/107759 | 11/2005 |

OTHER PUBLICATIONS

Shaikh et al., "Formulation and Evaluation of S-(-)-Amlodipine Besylate and Nebivolol Hydrochloride Tablets," J. Adv. Pharm. Tech. Res. vol. 1 (2), Apr.-Jun. 2010, pp. 199-206. (Year: 2010).*
Turner, Travis H., "*Measures of cognitive functioning as predictors of treatment outcome for cocaine dependence*", Journal of Substance Abuse Treatment, 37 (2009) 328-334.
Official Action, CN Appln. No. 201980072518.7, dated Jul. 6, 2008.
International Search Report for PCT/EP2019/077270 dated Dec. 6, 2019, 3 pages.
Written Opinion of the ISA for PCT/EP2019/077270 dated Dec. 6, 2019, 6 pages.
Tanner et al., "Production of Riboflavin by Fermentation", Feb. 2, 1951, pp. 759-764.
Mirza, S. et al; "Crystal Morphology Engineering of Pharmaceutical Solids: Tabletting Performance Enhancement", *AAPS PharmSciTech*, vol. 10, No. 1, Mar. 2009.
Chadha, R. et al; "Chrystal habit, characterization and pharmacological activity of various crystal form of arteether", *Acta Pharmaceutica Sinica B*, 2011; 1(2):129-135.
Jain, T. et al, "Effect of differential surface anisotropy on performance of two plate shaped crystals of aspirin form I", *European Journal of Pharmaceutical Sciences* 99 (2017) 318-327.
Bukovec, P. et al, "Effect of crystal habit on the dissolution behaviour of simvastatin crystals and its relationship to crystallization solvent properties", *Pharmazie* 71:263-268 (2016).
Shaikh, S.A. et al, "Formulation and Evaluation of S-(-)-Amlodipine Besylate and Nebivolol Hydrochloride Tablets", *J. Adv. Pharm. Tech. Res.*, vol. 1(2), Apr.-Jun. 2010.

* cited by examiner

*Primary Examiner* — Aradhana Sasan
(74) *Attorney, Agent, or Firm* — NIXON & VANDERHYE P.C.

(57) ABSTRACT

Antihypertensive agents which are crystalline having a general plate shape may be difficult to formulate as they often do not exhibit good flowability properties. Addition of spray-dried riboflavin surprisingly improves flowability of these agents.

8 Claims, 7 Drawing Sheets

FIGURE 3
FIGURE 3A:
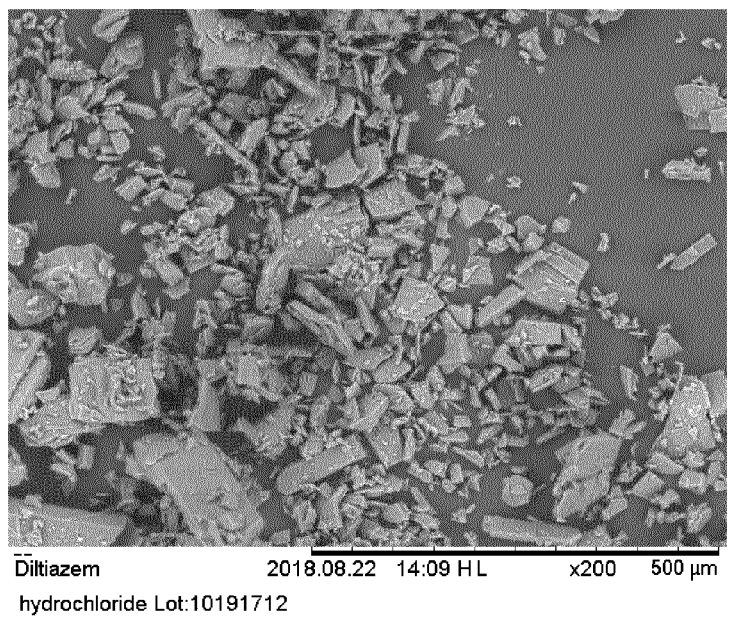
Diltiazem hydrochloride Lot:10191712
FIGURE 3B
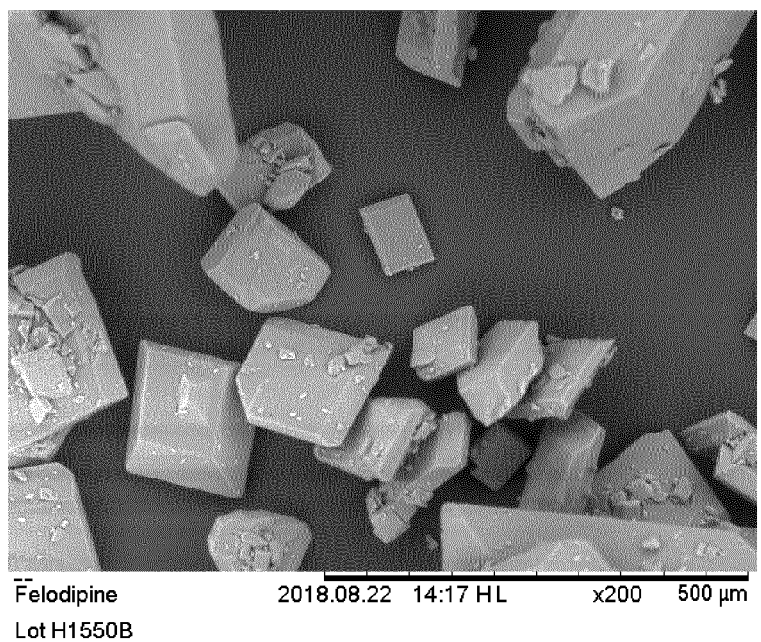
Felodipine Lot H1550B FIGURE 4
Figure 4 A
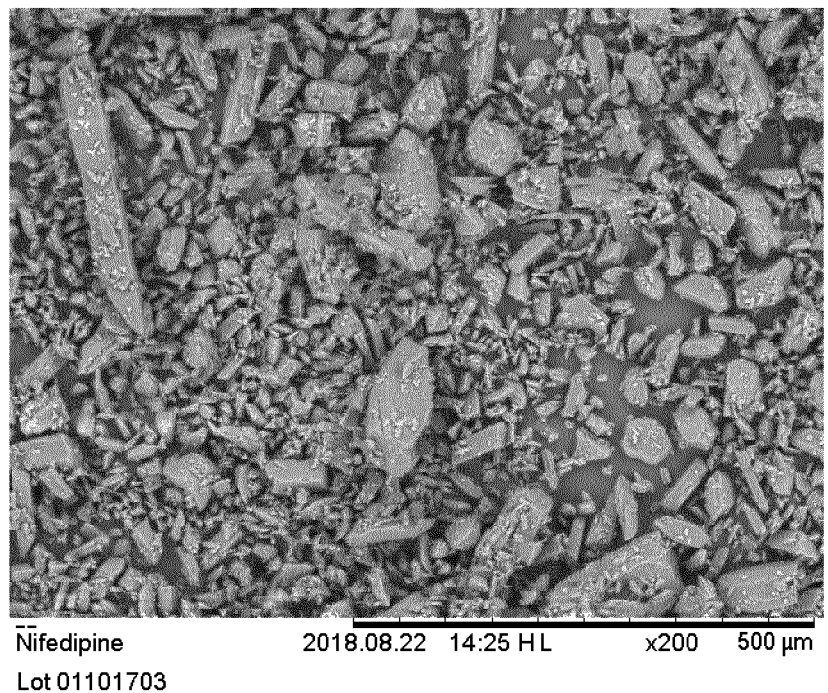
Nifedipine Lot 01101703
Figure 4b
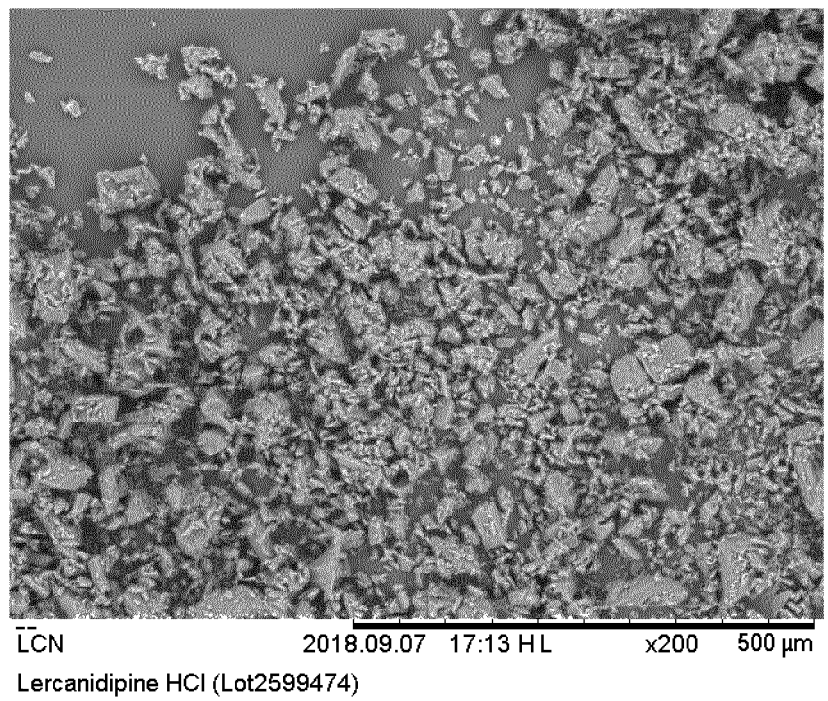
Lercanidipine HCl (Lot2599474)

FIGURE 5
Figure 5a
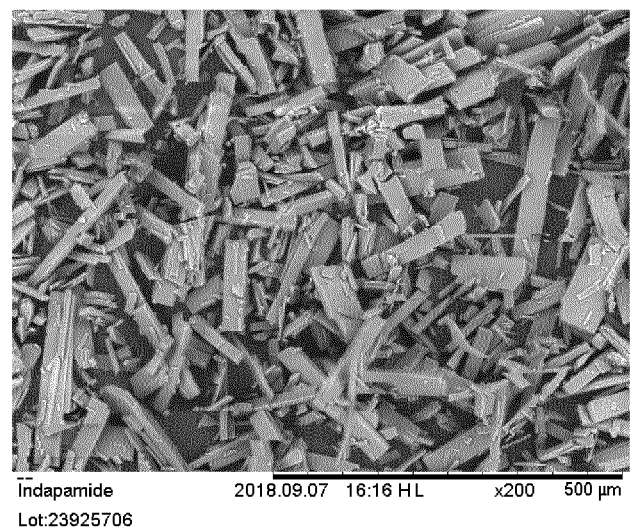
Indapamide   2018.09.07  16:16 H L    x200   500 µm
Lot:23925706
Figure 5b
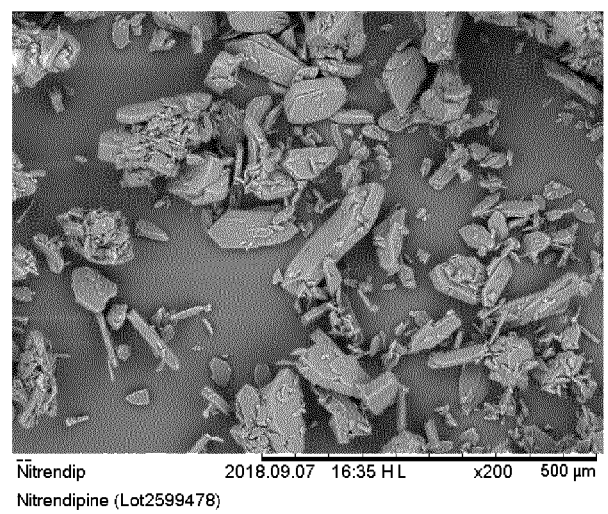
Nitrendip    2018.09.07  16:35 H L    x200   500 µm
Nitrendipine (Lot2599478)

MEDICAMENTS CONTAINING RIBOFLAVIN EXHIBITING IMPROVED FLOWABILITY

This application is the U.S. national phase of International Application No. PCT/EP2019/077270 filed Oct. 9, 2019 which designated the U.S. and claims priority to EP Patent Application No. 18204935.3 filed Nov. 7, 2018 and EP Patent Application No. 18204934.6 filed Nov. 7, 2018, the entire contents of each of which are hereby incorporated by reference.

BRIEF DESCRIPTION OF THE INVENTION

This invention is directed to compositions comprising an active ingredient which is composed of plate shaped crystals combined with riboflavin. Compositions with plate shaped crystals can exhibit impaired flowability, making them difficult to formulate into to final tablets or other forms suitable for medicaments. Spray dried riboflavin, when added to these active ingredients can increase their flowability.

BACKGROUND OF THE INVENTION

Many ingredients which have biological activity rendering them suitable as pharmaceuticals or nutraceuticals occur in crystal form. Crystals can take many shapes, due to the chemical composition of the substance and the method of purifying or crystallization used. If the crystals are configured in a plate like shape, i.e. generally rectangular and flattened, they can stick together, and thus cause difficulties when processing.

Numerous pharmaceutical compounds are known to treat hypertension, which fall into various classes. These include:
1) Angiotensin-converting enzyme (ACE) inhibitors. These work by interfering with the formation of angiotensin, a hormone which constricts blood vessels. This class includes marketed drugs such as enalapril, lisinopril, ramipril, perindopril and captopril.
2) Angiotensin II receptor blockers (ARBs). These function by blocking the action of angiotensin, but not its formation. Examples of marketed drugs in this class include: valsartan, losartan and others.
3) Beta blockers, also called beta-adrenergic blocking agents. These function by blocking the effects of the hormone epinephrine (adrenaline), which results in the heart beating slower and with less force. Examples of beta blockers include metoprolol, nadolol, atenolol and carvedilol.
4) Renin inhibitors. These slow the production of renin, an enzyme which is involved in a pathway leading to increase blood pressure. This includes aliskiren.
5) Calcium channel blockers slow the movement of calcium into the cells of the heart and blood vessel walls, making it easier for the heart to pump and widen blood vessels. Examples include amlodipine, diltiazem, felodipine, isradipine, nicardipine, nifedipine, nisoldipine, azelnidipine and verapamil.
6) Diuretics—these work by helping the kidneys excrete excess water, so there is less fluid in the blood vessels, thus reducing the pressure and making it easier for the heart to pump. Examples include: hydrochlorothiazide, chlorothiazide, indapamide and metolazone.

One of the problems in the manufacture of tablets, capsules, and/or other oral dosage forms of these medicaments is that their ingredients often do not exhibit good flowability, and thus may be difficult to manufacture. If flowability is poor, it is possible that the active ingredient is not homogeneously distributed throughout the final product. One solution to this problem is to add various glidants/and or other types of additives such as SiO2, magnesium silicate or talc to improve flowability. However, even with these additives, homogeneity may not be assured.

EP0272336 and U.S. Pat. No. 1,904,699 discuss nifedipine (a calcium antagonist), which is embedded in polyethylene glycol and 0.5-20% by weight Vitamin B2 based on the nifedipine and at least one surface active ingredient. The Vitamin B2 is present to impart UV light protection and solubility of the nifedipine. There is no teaching of using spray-dried riboflavin to improve flowability.

EP1048668 (Hoffmann La Roche) discloses a process for preparing spray-dried riboflavin.

U.S. Pat. No. 5,300,303 (BASF) also discloses a process for preparing riboflavin granules with no binder.

Shaikh et al 2007 *Asian J Pharmaceutics* 1(1):124-128 teaches formulations for amlodipine besylate, with improved dissolution properties.

It would be desirable to have anti-hypertensive medicaments which are also flowable powders.

DETAILED DESCRIPTION OF THE INVENTION

It has been found, in accordance with this invention, that a composition comprising the combination of a crystalline active ingredient and spray-dried riboflavin has increased flowability compared to a composition which comprises the active ingredient in the absence of riboflavin.

In one embodiment, the active ingredient comprises plate shaped crystals when observed under a microscope, and the active ingredient comprises at least 50% spheres and irregular spheres by volume as measured by a particle size and shape analyzing instrument such as a Malvern Morpho G3 instrument (combines optical microscopy and mathematical algorithms to determine both the 3-dimensional shape of particles, and their volume in the sample). Further, it is preferred that the riboflavin is a spray-dried riboflavin formulation, which is roughly spherical in shape when observed under a microscope.

In a specific preferred embodiment, the crystalline is an antihypertensive active ingredient which comprises plate shaped crystals when observed under a microscope, and the active ingredient comprises at least 50% spheres and irregular spheres by volume as measured by a particle size and shape analyzing instrument such as a Malvern Morpho G3 instrument (combines optical microscopy and mathematical algorithms to determine both the 3-dimensional shape of particles, and their volume in the sample).

Without wishing to be bound by theory, we believe that the impaired flowability could result from the crystal habit and the volume of various particle sizes of the antihypertensive active ingredient. Many active ingredients, regardless of their bioactivity, are known in the art to exist in crystal forms. The shape of the crystal, termed its "habit" can determine many of its properties which are important to the manufacture and formulation process. The crystal habit will depend on the methods and conditions used during the crystallization process. Thus, a single active ingredient may exhibit more than one crystal habit, depending on its manufacturing process.

A plate type crystal habit is described as one where the crystals have approximately the same length and width, but their height is much smaller than either their length or width. It is thought that this shape leads to difficulties in formulation and tableting. The crystal sizes of the active ingredient can vary. For example, one antihypertensive agent, amlodipine besylate, has a size distribution range of d(0.1) 10 µm, d(0.5) 150 µm and d(0.9) 500 µm.

Many active ingredients are known to have a plate-shaped crystalline form. The crystal habit is not limited to a particular class of drug (based on its biological activity). Examples of diverse active ingredients which can have plate shaped crystal forms include:
- Aspirin (acetyl salicylic acid) see, e.g. Jain et al 2017 *Eur J Pharma Sci* 99:318-327.
- Arteether, an anti-malarial drug; see, e.g. Chada et al 2011 *Acta Pharma Sinica B* 1(2):129-135.
- Erythromycin, an antibiotic; see e.g. Mirza et al 2009 *AAP PharmSCiTech* 19 (1) 113-119
- Simvastatin, an anti-cholesterol drug; see e.g. Bukovec et al *Pharmazie* 71: 263-268
- Various antihypertensive agents, including amlodipine (See FIG. 1).

An instrument such as a Malvern Morpho G3 uses image analysis to determine particle size and shape of a sample. The analytical technique is based on "image analysis" where a two-dimensional image of a 3-dimensional particle is captured and various size and shape parameters from a 2D image are calculated. This method can classify the particles as "spheres", "irregular spheres", "sticks" or "unclassified". Crystal particles which appear as generally plate-shaped under a microscope will be detected as "irregular spheres" or "unclassified" by this instrument.

It has been found in accordance with this invention that the shape of the spray-dried riboflavin, which is generally spherical, unexpectedly improved the flowability of the plate shaped crystals. In a preferred embodiment, the sum of the volume percentage of spheres and irregular spheres (as determined by image analysis such as described for a Malvern Morpho G3) is at least 50%. At percentages below 50%, the addition of riboflavin to the plate shaped crystals may not significantly improve their flowability. The spray-dried riboflavin particles preferably have a distribution range sized as d(0.1) 30 µm, d(0.5) 80 µm and d(0.9) 150 µm, when measured using laser diffraction at the pressure of 0.1 bar (e.g. Malvern Mastersizer 2000).

Alternatively, in the absence of a particle size and shape measuring device as described above, one can test to see if the active ingredient contains at least 50 volume % spheres and irregular spheres by comparing the flowability rates prior to and after the addition of riboflavin. If the rate of flow is improved by the addition of riboflavin, then the active ingredient comprises as least 50 volume % spheres and irregular spheres.

In another test, the active ingredient may be examined under a microscope to determine if plate-shaped crystals may be observed. If so, then the flowability rates of the active ingredient in the presence and absence of spray-dried riboflavin can be determined. If the flowability in the presence of riboflavin is improved, then the active ingredient may be considered to comprise at least 50 volume % spheres and irregular spheres.

Thus, another aspect of this invention is a method of improving flowability of an active ingredient comprising the steps of:
a) mixing the active ingredient with spray-dried riboflavin to obtain a composition comprising active ingredient and spray-dried riboflavin;
b) determining the flow rate of the composition of step a); and
c) comparing the flow rate of the composition of step a) to the flow rate of the active ingredient in the absence of riboflavin to determine if there is an improved flowability.

Thus, another aspect of this invention is a method of improving flowability of an antihypertensive agent comprising the steps of:
a) mixing the antihypertensive agent with spray-dried riboflavin to obtain a composition comprising antihypertensive agent and spray-dried riboflavin;
b) determining the flow rate of the composition of step a); and
c) comparing the flow rate of the composition of step a) to the flow rate of the antihypertensive agent in the absence of riboflavin to determine if there is an improved flowability.

Flowability can be determined by any standard method. Both the crystal size distribution and the spray-dried riboflavin particle size distribution supra were analysed using Malvern Mastersizer 2000 (Worcestershire, UK). The Malvern Mastersizer uses the principles of static light scattering (SLS) to calculate the size of particles in a sample. The measurements were done in triplicates using the pressure of 0.1 bar.

The antihypertensive active ingredient may be selected from the class of antihypertensive ingredients referred to as calcium channel blockers. More preferably it is selected from the group consisting of amlodipine, diltiazem, felodipine, iradipine, nicardipine, nifedipine, nisoldipine, lercanidipine, nitrendipine, azelnidipine, verapamil and a pharmaceutically acceptable salt thereof the aforementioned calcium channel blockers. In another embodiment it is a diuretic such as hydrochlorothiazide. In another embodiment it is enalapril. In another embodiment it is atenolol.

In some preferred embodiments it is amlodipine, felodipine, hydrochlorothiazide, enalapril or atenolol. In some preferred embodiments it is amlodipine besylate. Amlodipine is commercially available under the brand names ISTIN and AMLOSTIN, and NORVASC.

The riboflavin used in this combination is preferably a spray-dried formulation of riboflavin. In more preferred embodiments it has a generally spherical shape such as that shown in FIG. 2. One such formulation is sold under the trademark RIBOFLAVIN UNIVERSAL available from DSM Nutritional Products, Switzerland. In preferred embodiments, the riboflavin in manufactured under conditions that are considered appropriate for regulatory certification for use in a pharmaceutical product.

The ratio of the riboflavin to the antihypertensive active ingredient according to this invention is typically from 1:10 to 10:1 based on the weight percentage of the antihypertensive active ingredient and the spray-dried riboflavin. Surprisingly we have found that while riboflavin improves flowability at all ratios, there are some ratios where more antihypertensive product than riboflavin has the best flowability. Preferably the ratio of riboflavin to antihypertensive active ingredient ranges from 1:5 to 5:1. In some preferred embodiments it is 1:1. In another preferred embodiments it is 1:4.

Dosages

The active ingredient is used at a dosage which is known in the art for its intended use.

The antihypertensive active ingredient should be given at a dosage which is known in the art. For example, amlodipine is generally available in a tablet form containing 2.5 mg, 5 mg and 10 mg active. The amount of riboflavin is thus calculated accordingly using the ratios above, so for 2.5 mg amlodipine, the amount of riboflavin can be 0.5 to 12.5 mg.

BRIEF DESCRIPTION OF THE FIGURES

FIG. 3 has electron micrographs of two calcium channel blocker crystals. FIG. 3a is diltiazem, FIG. 3B is felodipine. Both are magnification 200×

FIG. 4 has electron micrographs of two calcium channel blocker crystals. FIG. 4a is nifedipine; FIG. 4b is lercanidipine. Magnification 200×.

FIG. 5 has electron micrographs of crystals. FIG. 5a is indapamide, (a diuretic), and FIG. 5 b is nitrendipine, a calcium channel blocker. Magnification is 200×

Figure 1:
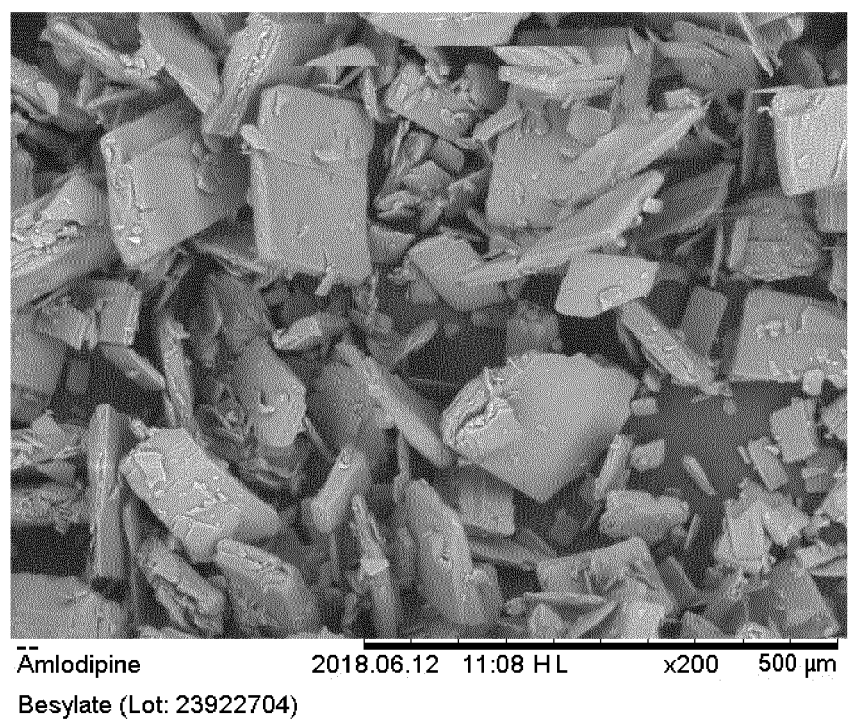
FIG. 1 is an electron micrograph of amlodipine besylate crystals, a calcium channel blocker (magnification of 200×).
Figure 2:
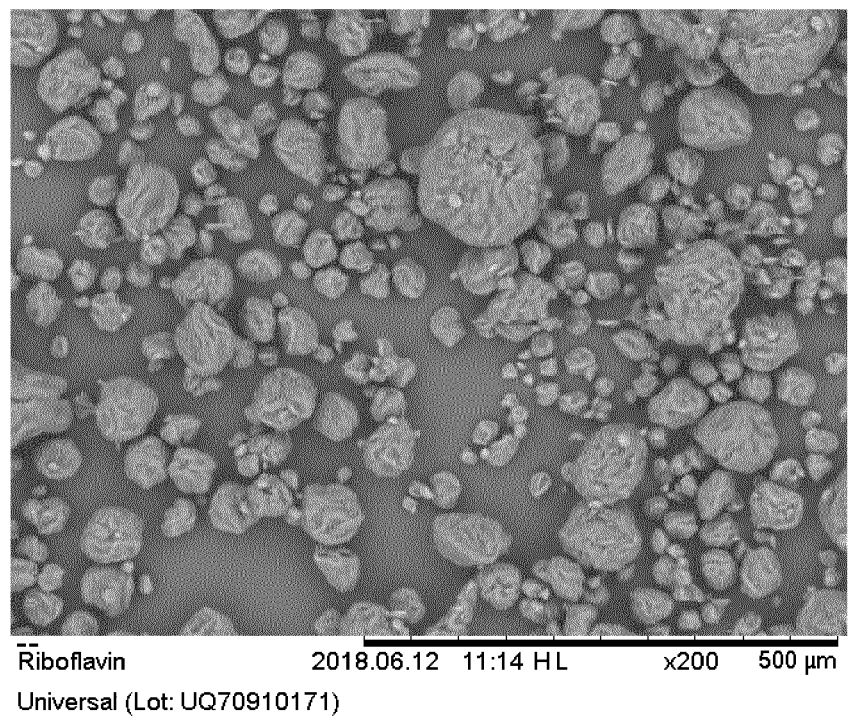
FIG. 2 is an electron micrograph of spray-dried riboflavin magnification 200×.
Figure 6:
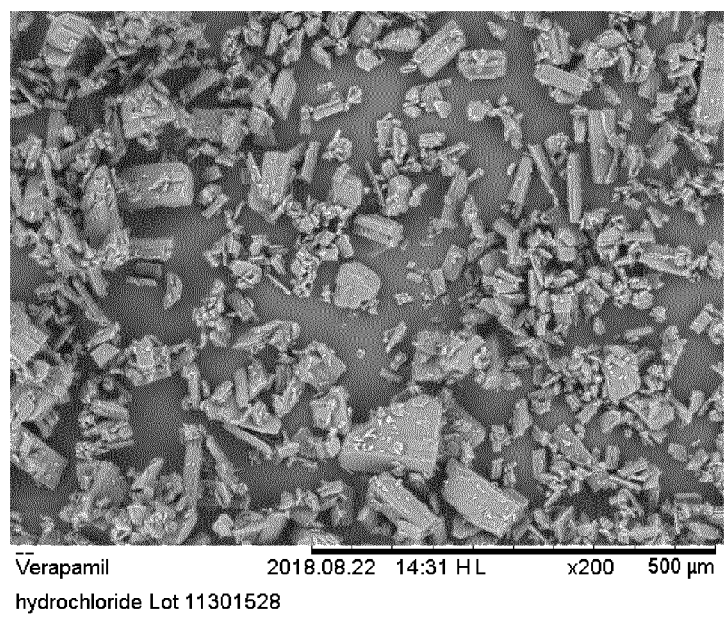
FIG. 6 a has an electron micrograph of verapamil hydrochloride, a calcium channel blocker. Magnification is 200×.
Figure 7:
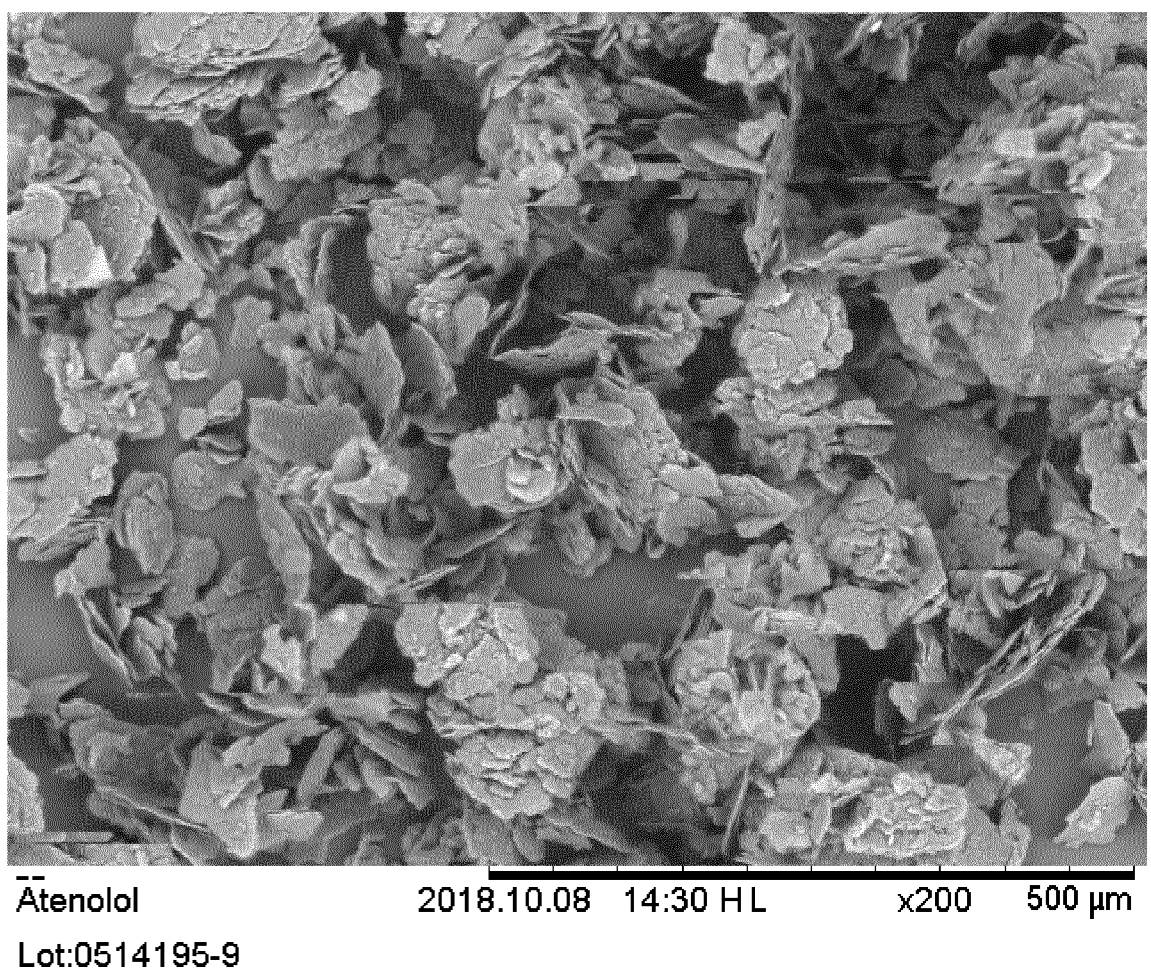
FIG. 7 has an electron micrograph of a beta blocker atenolol.

The antihypertensive agent such as amlodipine or a pharmaceutically acceptable salt and spray-dried riboflavin composition of this invention may be formulated into any type of oral formulation; preferred formulations include tablets, capsules, and the like using known methods and known formulation additives.

The composition comprising the crystalline antihypertensive agent may be produced by simply mixing the crystalline antihypertensive agent and the spray-dried riboflavin. In some embodiments, amlodipine having a plate shaped crystalline habit is mixed with spray-dried riboflavin.

The following non-limiting Examples are presented to better illustrate the invention.

EXAMPLES

Example 1

Methods

Scanning Electron Microscopy (SEM)

The morphology of tested materials was analyzed using Scanning Electron Microscope (TM 3030, Hitachi, Tokyo, Japan) with the magnification of 200.

Flowability

The powder flowability was determined with a Pharmatest PTG-S4 automated powder characterization instrument (Pharma Test Apparatebau AG, Hamburg, Germany). This system measures the flow behavior of granules and powders in compliance with the current EP <2.9.36/17> and USP <1174> pharmacopoeia, as well as, with the international ISO 4324 standards.

Mass flow rate (g/min) was determined via the method of flow through an orifice. Flow rate is interpreted as the time needed for a specified amount of powder (10 g) to flow through an orifice with different diameters. A free-flowing powder should be able to flow through the whole set of diameters 5, 7, 9 and 10 mm. The plot of flow rate vs. orifice diameter is referred as flow curve. Three parallel measurements were performed to determine the flow rate. Results are presented in Table 1

TABLE 1

| Product | Weight (g) | | mm | mm | 7 mm | 5 mm |
|---|---|---|---|---|---|---|
| [/1] Riboflavin Universal (UQ70910171) | 10.0 | Time [sec] | 13.6 | 12.0 | 24.1 | * |
| | | Rotation [rpm] | 0 | 0 | 0 | 0 |
| | | Flowrate | 44 g/min | 50 g/min | 25 g/min | 0 g/min |
| [/2] 1:1 Mix of Ribo.Univ./ Amlodipine Besylate | 10.0 | Time [sec] | 5.5 | 5.8 | 13.6 | * |
| | | Rotation [rpm] | 0 | 0 | 0 | 0 |
| | | Flowrate | 109 g/min | 103 g/min | 44 g/min | 0 g/min |
| [/3] Amlodipine Besylate | 10.0 | Time [sec] | * | * | * | * |
| | | Rotation [rpm] | 0 | 0 | 0 | 0 |
| | | Flowrate | 0 g/min | 0 g/min | 0 g/min | 0 g/min |
| [/4] 1:4 Mix of Ribo.Univ./ Amlodipine Besylate | 10.0 | Time [sec] | 3.0 | 4.4 | 6.7 | 16.8 |
| | | Rotation [rpm] | 0 | 0 | 0 | 0 |
| | | Flowrate | 198 g/min | 135 g/min | 90 g/min | 36 g/min |

* Powder does not flow

Example 2

Following the same methods as outlined in Example 1, the flowability of hydrochlorothiazide, a diuretic was measured with and without spray-dried riboflavin. Results are presented in Table 2, below.

TABLE 2

| Product | Weight (g) | | 10 mm | 9 mm | 7 mm | 5 mm |
|---|---|---|---|---|---|---|
| [/1] Hydrochlorothiazide (2597487) | 10.0 | Time [sec] | * | * | * | * |
| | | Rotation (rpm) | 0 | 0 | 0 | 0 |

TABLE 2-continued

| Product | Weight (g) | | 10 mm | 9 mm | 7 mm | 5 mm |
|---|---|---|---|---|---|---|
| [/2] 1:1 Mix of Hydrochlorothiazide (2597487)/ B2 Universal (UQ70910171) | 10.0 | Flowrate | 0 g/min | 0 g/min | 0 g/min | 0 g/min |
| | | Time [sec] | 4.3 | 5.2 | * | * |
| | | Rotation (rpm) | 0 | 0 | 0 | 0 |
| | | Flowrate | 138 g/min | 115 g/min | 0 g/min | 0 g/min |

* Powder does not flow

Example 3

Following the same methods as outlined in Example 1, the flowability of enalapril, an ACE inhibitor was measured with and without spray-dried riboflavin. Results are presented in Table 3, below.

TABLE 3

| Product | Weight (g) | | 10 mm | 9 mm | 7 mm | 5 mm |
|---|---|---|---|---|---|---|
| [/1] Enalapril (maleate) (0497851-2) | 10.0 | Time [sec] | * | * | * | * |
| | | Rotation (rpm) | 0 | 0 | 0 | 0 |
| | | Flowrate | 0 g/min | 0 g/min | 0 g/min | 0 g/min |
| [/2] 1:1 Mix of B2 Universal/Enalapril | 10.0 | Time [sec] | 6.3 | 6.7 | 11.8 | 57.8 |
| | | Rotation (rpm) | 0 | 0 | 0 | 0 |
| | | Flowrate | 96 g/min | 90 g/min | 51 g/min | 10 g/min |
| [/3] 1:3 Mix of B2 Universal/Enalapril | 10.0 | Time [sec] | 6.2 | 9.9 | 15.5 | * |
| | | Rotation (rpm) | 0 | 0 | 0 | 0 |
| | | Flowrate | 97 g/min | 61 g/min | 39 g/min | 0 g/min |

* Powder does not flow

Example 4

Following the same methods as outlined in Example 1, the flowability of atenolol, a beta blocker was measured with and without spray-dried riboflavin. Results are presented in Table 4, below.

TABLE 4

| Product | Weight (g) | | 10 mm | 9 mm | 7 mm | 5 mm |
|---|---|---|---|---|---|---|
| [/1] Atenolol (0514195-9) | 10.0 | Time [sec] | * | * | * | * |
| | | Rotation (rpm) | 0 | 0 | 0 | 0 |
| | | Flowrate | 0 g/min | 0 g/min | 0 g/min | 0 g/min |
| [/2] 1:1 Mix of B2 Universal/Atenolol | 10.0 | Time [sec] | 5.3 | 4.6 | 19.4 | * |
| | | Rotation (rpm) | 0 | 0 | 0 | 0 |
| | | Flowrate | 114 g/min | 130 g/min | 31 g/min | 0 g/min |
| [/3] 1:2 Mix of B2 Universal/Atenolol | 10.0 | Time [sec] | 3.3 | 5.3 | 16.7 | * |
| | | Rotation (rpm) | 0 | 0 | 0 | 0 |
| | | Flowrate | 184 g/min | 113 g/min | 36 g/min | 0 g/min |

* Powder does not flow

Example 5

Comparative Examples

Using methods as described above in Examples 1, 2, 3 and 4 crystals of various antihypertensive drugs were mixed with riboflavin. Results are presented below:

TABLE 5

Morphology vs flowability improvement

| Compound | Plate-shaped crystal morphology | Improved Flowability with Riboflavin |
|---|---|---|
| Calcium Channel Inhibitors | | |
| Amlodipine Besylate | Yes | YES |
| Nifedipine | Yes | No |

TABLE 5-continued

Morphology vs flowability improvement

| Compound | Plate-shaped crystal morphology | Improved Flowability with Riboflavin |
|---|---|---|
| Felodipine | Yes | YES |
| Nitrendipine | Yes | No |
| Angiotensin Receptor Blockers (ARB) | | |
| Candesartan Cilexetil | no | no |
| Olmesartan | no | no |
| Valsartan | no | no |
| Diuretics | | |
| Hydrochlortiazide | Yes | YES |
| Indapaminde | yes | No |
| ACE inhibitors | | |
| Enalapril | Yes | YES |
| Beta-blockers | | |
| Metoprolol Tartate | No | no |
| Carvediol | Yes | no |
| Atenolol | Yes | YES |

Example 6

Compounds from Example 5 which showed improved flowability were further examined for particle size using the Malvern Morpho G3 instrument. "Vol.M.M" reflect the size of those particles which constitute the bulk of the sample volume. Particle sizes were measured and results are shown below. d(0.1) presents the diameter of 10% of all particles, d(0.5) is the diameter of 50% of all particles and d(0.9) presents the diameter of 90% of the particles in the sample.

Amlodipine besylate:
d(0.1)=25 µm
d(0.5)=72 µm
d(0.9)=163 µm
Vol.M.M d(4,3): 87 µm Felodipine
d(0.1)=147 µm
d(0.5)=320 µm
d(0.9)=478 µm
Vol.M.M d(4,3): 325 µm Hydrochlortiazide
d(0.1)=123 µm
d(0.5)=319 µm
d(0.9)=551 µm
Vol. M.M. d(4.3): 337 µm Enalapril
d(0.1)=32 µm
d(0.5)=129 µm
d(0.9)=304 µm
Vol.M.M. d(4,3): 157 µm Atenolol
d(0.1)=36 µm
d(0.5)=100 µm
d(0.9)=218 µm
Vol.M.M d(4,3): 117 µm Riboflavin Universal
d(0.1)=44 µm
d(0.5)=93 µm
d(0.9)=172 µm
Vol.M.M d(4,3): 106 µm Results: all of the compounds where the percentage of the sum of the sphered/irregular sphered is at least 50% showed improved flowability. Amlodipine was 60%, felodipine was 65%, hydrochlorothiazide was 74%, enalapril was 78% and atenolol 53%. Riboflavin universal was 95%. On the other hand, if the percentage of the sum of the spheres/irregular spheres was less than 50%, then riboflavin did not improve flowability. This was observed for diltiazem 32%, nitrendipine 31%, Indapaminde 13% and Valsartan 39%.

The invention claimed is:

1. A composition comprising:
    a) an active ingredient which comprises at least 50% plate shaped crystals when observed under a microscope, and the active ingredient comprises at least 50% spheres and irregular spheres by volume as measured by a particle size and shape analyzing instrument; and
    b) spray-dried riboflavin.

2. The composition according to claim 1, wherein the active ingredient and the spray-dried riboflavin are present in a weight ratio between the active ingredient and the spray-dried riboflavin of 10:1 to 1:10.

3. The composition according to claim 1, wherein the active ingredient is an antihypertensive agent.

4. The composition according to claim 3, wherein the antihypertensive agent is a calcium channel blocker.

5. The composition according to claim 4, wherein the calcium channel blocker is selected from the group consisting of: amlodipine, diltiazem, felodipine, iradipine, nicardipine, nifedipine, nisoldipine, lercanidipine, nitrendipine, azelnidipine, verapamil and a pharmaceutically acceptable salt thereof the aforementioned calcium channel blockers.

6. The composition according to claim 4, wherein the calcium channel blocker is amlodipine or amlodipine besylate.

7. An oral formulation comprising the composition of claim 1, wherein the oral formulation is in a form of a tablet, a capsule, or a powder.

8. A method of improving flowability of an active ingredient comprising the steps of:
    a) mixing the active ingredient with spray-dried riboflavin to obtain a flowable composition comprising the active ingredient and the spray-dried riboflavin;
    b) determining a flow rate of the flowable composition of step a); and
    c) comparing the flow rate of the composition of step a) to a flow rate of the active ingredient in the absence of spray-dried riboflavin to determine if there is an improved flowability.

* * * * *